US007419505B2

(12) United States Patent  (10) Patent No.: US 7,419,505 B2
Fleischmann et al.  (45) Date of Patent: Sep. 2, 2008

(54) COLLAPSIBLE, ROTATABLE, AND TILTABLE HYDRAULIC SPINAL DISC PROSTHESIS SYSTEM WITH SELECTABLE MODULAR COMPONENTS

(76) Inventors: Lewis W. Fleischmann, 9004 Pittsfield Rd., Pikesville, MD (US) 21208-1010; Christopher Galuardi, 35 Latimore Way, Owings Mills, MD (US) 21117

( * ) Notice: Subject to any disclaimer, the term of this patent is extended or adjusted under 35 U.S.C. 154(b) by 103 days.

(21) Appl. No.: 11/110,893

(22) Filed: Apr. 21, 2005

(65) Prior Publication Data

US 2005/0216084 A1    Sep. 29, 2005

Related U.S. Application Data

(63) Continuation-in-part of application No. 10/419,899, filed on Apr. 22, 2003, now Pat. No. 6,981,989.

(51) Int. Cl.
  *A61F 2/44* (2006.01)
(52) U.S. Cl. ...................... 623/17.11; 606/99
(58) Field of Classification Search ............. 606/61, 606/99; 623/17.11–17.16
See application file for complete search history.

(56) References Cited

U.S. PATENT DOCUMENTS

| | | | |
|---|---|---|---|
| 3,867,728 A | 2/1975 | Stubstad et al. | |
| 3,875,595 A | 4/1975 | Froning | |
| 4,349,921 A | 9/1982 | Kuntz | |
| 4,904,260 A | 2/1990 | Ray et al. | |
| 4,932,975 A * | 6/1990 | Main et al. ............... | 623/17.12 |
| 4,946,378 A | 8/1990 | Hirayama et al. | |
| 5,002,576 A | 3/1991 | Fuhrmann et al. | |
| 5,071,437 A | 12/1991 | Steffee | |
| 5,171,278 A | 12/1992 | Pisharodi | |
| 5,171,280 A | 12/1992 | Baumgartner | |

(Continued)

FOREIGN PATENT DOCUMENTS

DE    4213771 C1    9/1993

(Continued)

OTHER PUBLICATIONS

"Ceramic Skate Wheel Bearings", http://skatelog.com/bearings/ceramic.htm.

*Primary Examiner*—Eduardo C. Robert
*Assistant Examiner*—Michael J. Araj
(74) *Attorney, Agent, or Firm*—Rosenberg, Klein & Lee

(57) ABSTRACT

A modular hydraulic spinal intervertebral prosthetic device offering individualized optimization of an implantable disc prosthesis by having selectable crown plates modules with differing lordosis angles and differing cross-sectional profiles, and selectable bellows cartridges having differing load-bearing capabilities. The device offers substantially full physiological degrees of motion, and by the incorporation of both a dashpot mechanism and a biasing element within reversibly displaceable and tiltable bellows provides hydraulic load bearing capability. The bellows assembly is advantageously pre-loaded to sub-atmospheric pressure. The dashpot further increases resistance to lateral sheer loading beyond the bellows convolutions acting alone. Rotational coupling of the upper crown plate and center bearings plate permits normal twisting movements, and spinal flexural freedom is provided by the bellows interposed between the center bearings plate and the lower end plate. The bellows also provides a hermetic seal which prevents any wear debris from migrating to the surrounding body tissue.

16 Claims, 11 Drawing Sheets

U.S. PATENT DOCUMENTS

| | | |
|---|---|---|
| 5,192,327 A | 3/1993 | Brantigan |
| 5,236,460 A | 8/1993 | Barber |
| 5,246,458 A | 9/1993 | Graham |
| 5,306,307 A | 4/1994 | Senter et al. |
| 5,306,309 A | 4/1994 | Wagner et al. |
| 5,344,459 A | 9/1994 | Swartz |
| 5,401,269 A | 3/1995 | Buttner-Janz et al. |
| 5,458,642 A | 10/1995 | Beer et al. |
| 5,534,029 A | 7/1996 | Shima |
| 5,534,030 A | 7/1996 | Navarro et al. |
| 5,571,189 A | 11/1996 | Kuslich |
| 5,645,596 A | 7/1997 | Kim et al. |
| 5,645,597 A | 7/1997 | Krapiva |
| 5,674,296 A | 10/1997 | Bryan et al. |
| 5,676,701 A | 10/1997 | Yuan et al. |
| 5,755,807 A | 5/1998 | Anstaett et al. |
| 5,772,661 A | 6/1998 | Michelson |
| 5,824,094 A | 10/1998 | Serhan et al. |
| 5,827,328 A | 10/1998 | Buttermann |
| 5,860,973 A | 1/1999 | Michelson |
| 5,865,845 A | 2/1999 | Thalgott |
| 5,865,848 A | 2/1999 | Baker |
| 5,919,235 A | 7/1999 | Husson et al. |
| 6,001,130 A | 12/1999 | Bryan et al. |
| 6,004,326 A | 12/1999 | Castro et al. |
| 6,022,376 A | 2/2000 | Assell et al. |
| 6,039,763 A | 3/2000 | Shelokov |
| 6,066,154 A | 5/2000 | Reiley et al. |
| 6,083,225 A | 7/2000 | Winslow et al. |
| 6,096,038 A | 8/2000 | Michelson |
| 6,110,210 A | 8/2000 | Norton et al. |
| 6,113,599 A | 9/2000 | Landsberger |
| 6,113,637 A | 9/2000 | Gill et al. |
| 6,132,465 A | 10/2000 | Ray et al. |
| 6,139,579 A | 10/2000 | Steffee et al. |
| 6,146,422 A | 11/2000 | Lawson |
| 6,149,650 A | 11/2000 | Michelson |
| 6,156,067 A | 12/2000 | Bryan et al. |
| 6,162,252 A | 12/2000 | Kuras et al. |
| 6,187,048 B1 | 2/2001 | Milner et al. |
| 6,206,922 B1 | 3/2001 | Zdeblick et al. |
| 6,224,595 B1 | 5/2001 | Michelson |
| 6,241,769 B1 | 6/2001 | Nicholson et al. |
| 6,264,656 B1 | 7/2001 | Michelson |
| 6,267,763 B1 | 7/2001 | Castro |
| 6,270,498 B1 | 8/2001 | Michelson |
| 6,299,590 B1 | 10/2001 | Lüscher et al. |
| 6,302,914 B1 | 10/2001 | Michelson |
| 6,340,363 B1 | 1/2002 | Bolger et al. |
| 6,368,350 B1 | 4/2002 | Erickson et al. |
| 6,375,682 B1 | 4/2002 | Fleischmann et al. |
| 6,395,032 B1 | 5/2002 | Gauchet |
| 6,395,034 B1 | 5/2002 | Suddaby |
| 6,402,785 B1 | 6/2002 | Zdeblick et al. |
| 6,419,703 B1 | 7/2002 | Fallin et al. |
| 6,419,704 B1 | 7/2002 | Ferree |
| 6,447,544 B1 | 9/2002 | Michelson |
| 6,458,159 B1 | 10/2002 | Thalgott |
| 6,482,233 B1 | 11/2002 | Aebi et al. |
| 6,482,234 B1 | 11/2002 | Weber et al. |
| 6,527,806 B2 | 3/2003 | Ralph et al. |
| 6,540,785 B1 | 4/2003 | Gill et al. |
| 6,558,386 B1 | 5/2003 | Cragg |
| 6,565,606 B1 | 5/2003 | Bruce et al. |
| 6,579,320 B1 * | 6/2003 | Gauchet et al. .......... 623/17.15 |
| 6,582,466 B1 * | 6/2003 | Gauchet ................. 623/17.11 |
| 6,602,291 B1 | 8/2003 | Ray et al. |
| 6,607,558 B2 | 8/2003 | Kuras |
| 6,620,196 B1 | 9/2003 | Trieu |
| 6,679,915 B1 | 1/2004 | Cauthen |
| 6,706,068 B2 | 3/2004 | Ferree |
| 6,730,020 B2 | 5/2004 | Peng et al. |
| 6,733,534 B2 | 5/2004 | Sherman |
| 6,740,118 B2 | 5/2004 | Eisermann et al. |
| 6,749,636 B2 | 6/2004 | Michelson |
| 6,770,074 B2 | 8/2004 | Michelson |
| 6,808,538 B2 | 10/2004 | Paponneau |
| 6,835,208 B2 | 12/2004 | Marchosky |
| 2005/0038511 A1 | 2/2005 | Martz et al. |

FOREIGN PATENT DOCUMENTS

| | | |
|---|---|---|
| EP | 305723 A2 | 3/1989 |
| FR | 2734148 A1 | 12/1996 |
| WO | WO 9911203 A1 | 3/1999 |

* cited by examiner

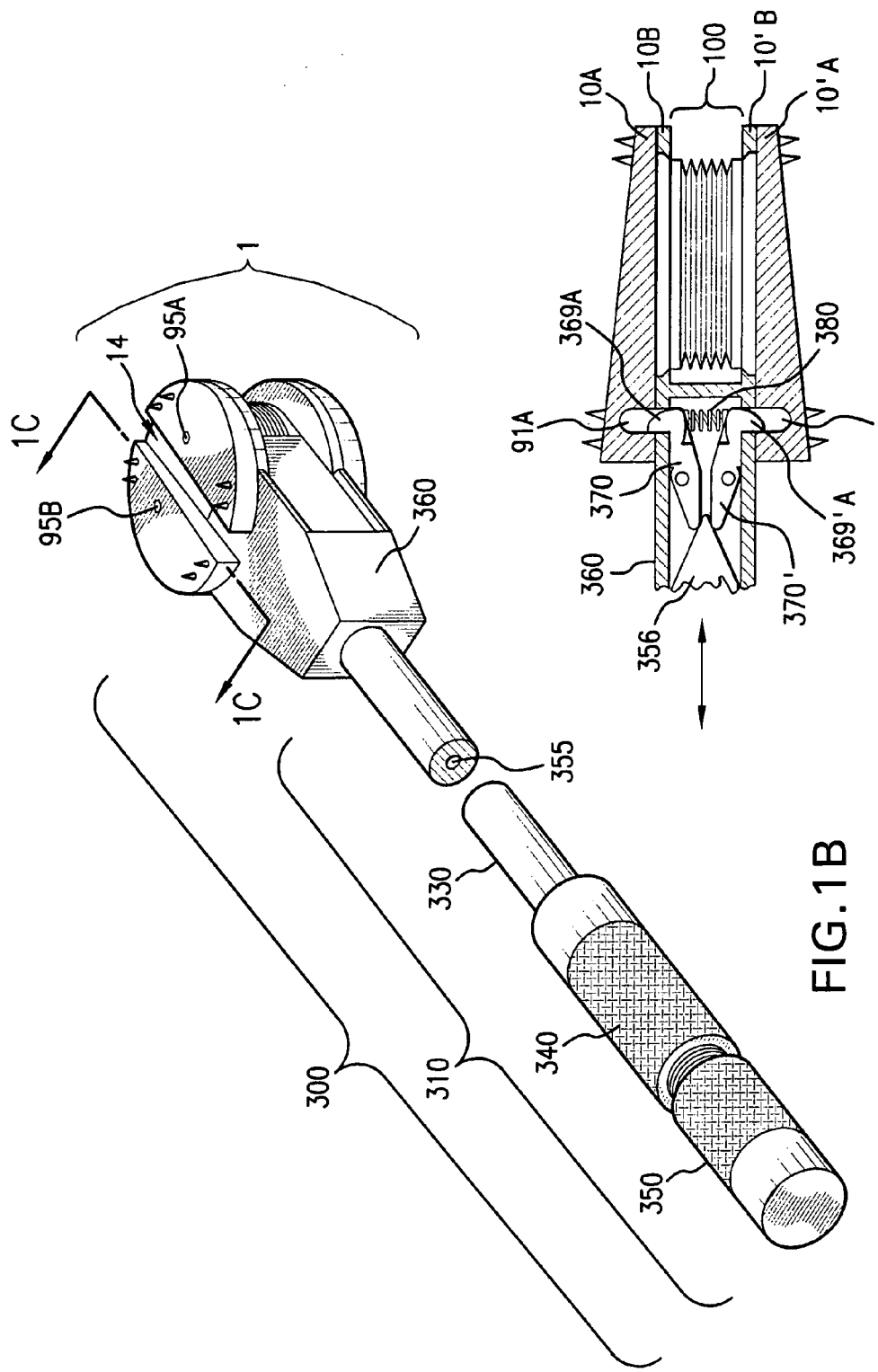

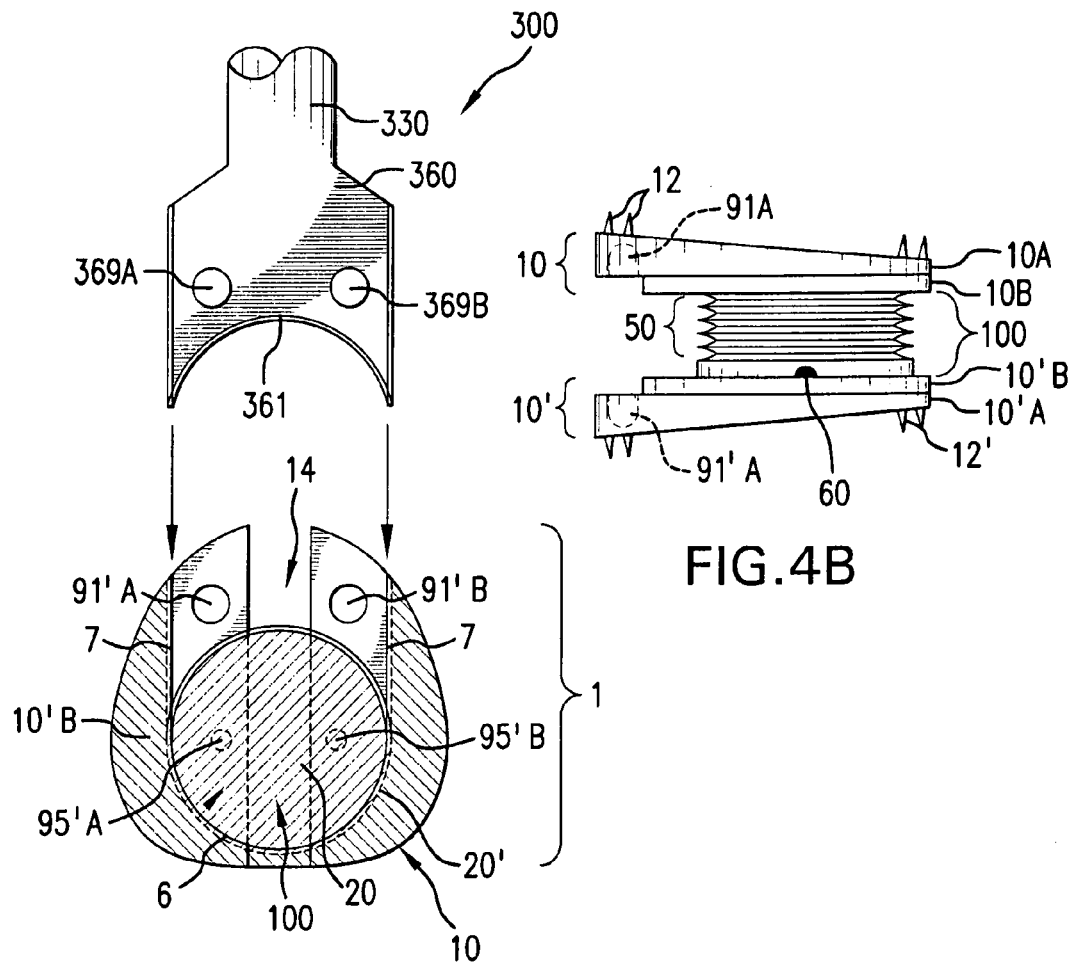
FIG.4B
FIG.4A
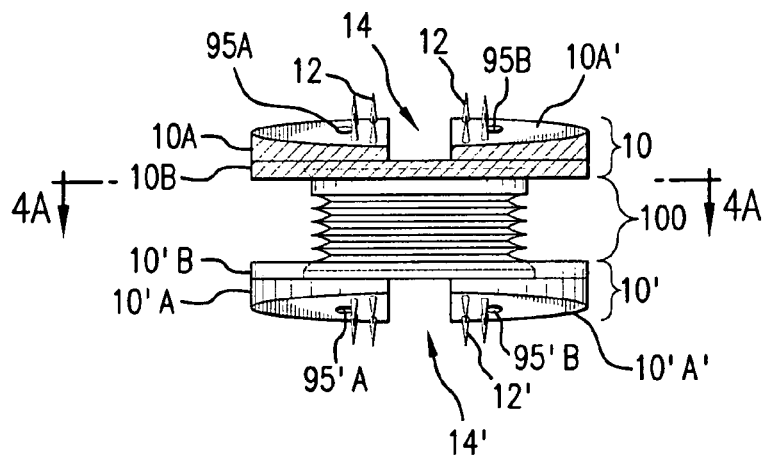
FIG.4C

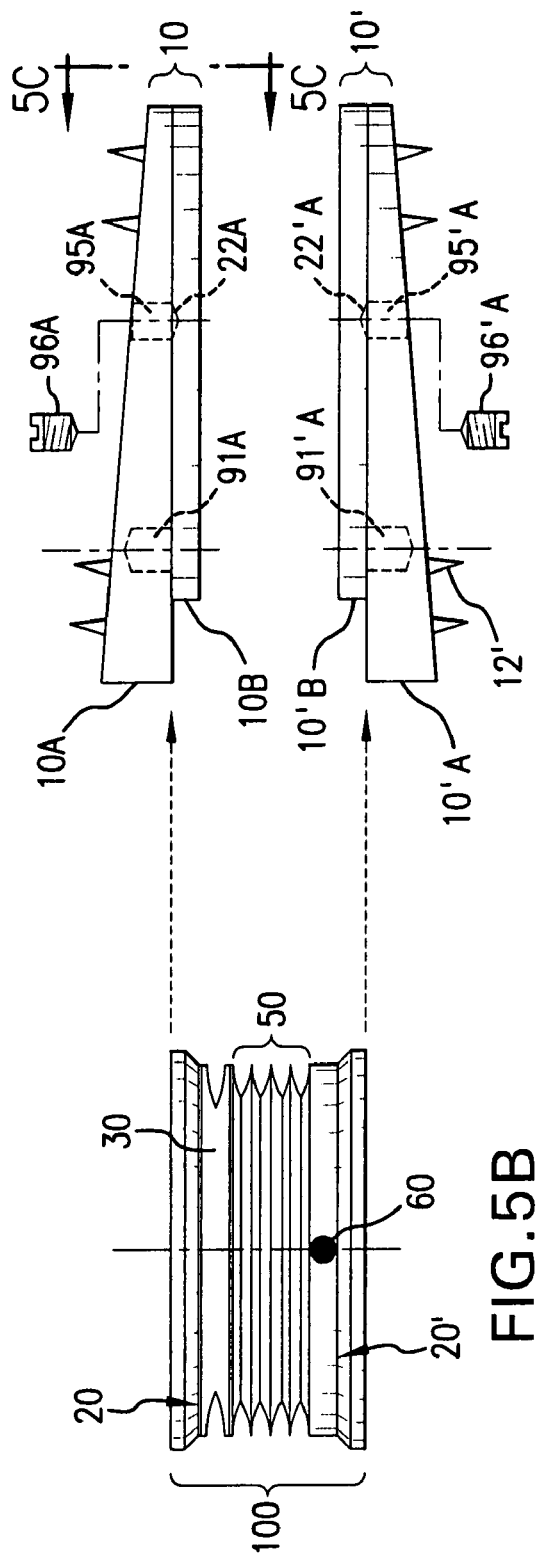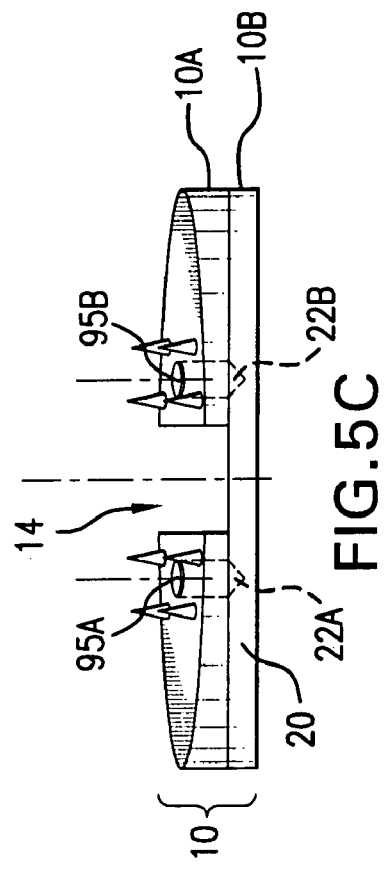

COLLAPSIBLE, ROTATABLE, AND TILTABLE HYDRAULIC SPINAL DISC PROSTHESIS SYSTEM WITH SELECTABLE MODULAR COMPONENTS

RELATED PATENTS

This application is a Continuation-in-Part of application Ser. No. 10/419,899 that was filed on 22 Apr. 2003 now U.S. Pat. No. 6,981,989.

FIELD OF INVENTION

The subject invention relates to a compressible, rotatable and tiltable spinal hydraulic prosthesis device and system for implantation of an individualized spinal disc prosthesis assembly to replace a degenerated disc in an intervertebral level of the spine. In particular, the present invention directs itself to a modular spinal prosthesis assembly formed of selectable components, the components allowing optimal individualization of the spinal disc prosthesis for a particular patient. Furthermore, the present invention is directed to a spinal disc prosthesis comprising a bio-compatible metallic bellows formed from a plurality of rigid washer-like members to minimize shear and lateral movements, filled with a non-compressible fluid and a compressible fluid, and permitting compression and tilting movements. Additionally, the bellows contain other axial load dampening mechanisms, including a dash pot mechanism and at least one biasing member.

More particularly, the invention directs itself to a modular spinal prosthesis assembly comprising a pair of opposing selectable crown plates having a selectable bellows cartridge interposed, with the assembly permitting rotation of the two vertebrae adjacent to the prosthesis relative to each other.

The invention further directs itself to an implantable modular spinal prosthetic device having selectable cross-sectional profiles, selectable angles of lordosis, and selectable load-bearing capacities. By the appropriate selection of modular components, the compressible, rotatable and tiltable spinal hydraulic prosthetic device assembly implanted in a particular patient at a particular spinal level is optimized.

BACKGROUND OF THE INVENTION

Implantable spinal prosthetic devices are well known in the art. Presently, the primary method used to remediate severe disc disease, spinal instability, discogenic pain, and/or spinal stenosis, is by surgical spinal fusion. In the spinal fusion procedure, two or more adjacent vertebrae are displaced, the spinal discs in between the vertebrae are removed by dissection, and crushed bone material is inserted between the two vertebrae; the bony material promotes the growth of new bone in the intervertebral space. The bony fusion material may be harvested intra-operatively from the patient's iliac crest or, alternatively, banked bone may be used. Since the fusion depends upon the ingrowth of new bone which takes months, mechanical means are necessarily incorporated at the time of surgery to maintain the stability and proper spacing between the vertebrae so as to permit the patient to carry normal loads imposed on the patient's spine during normal activities. Once the affected vertebrae are fused, that spinal segment will no longer take part in normal flexing, extending and twisting movements; higher stress loads will subsequently be imposed on discs and vertebra above and below the fused vertebral segment, often leading to the patient developing transition syndrome.

An important goal of spinal disc prosthesis implantations is to obviate the loss of normal biomechanics and range of motion associated with surgical fusion of a diseased spinal segment. Lordosis is an important element of the biomechanics of the spine, especially in the lumbar spine. While the lumbar vertebrae could be articulated in such a way that they form a straight vertebral column, this is not the shape assumed by the normal lumbar spine when a person is in the upright posture. This is because the sacrum, on which the lumbar spine rests, tilts forward so that its upper surface is inclined downwards and forwards. The size of this angle, with respect to a horizontal plane of the body, has a value in the range of about 40-45 degrees and increases by about 8 degrees upon standing. A straight lumbar spine would have to be inclined forward to articulate with the sacrum. In order to restore a normal upward orientation and to compensate for the normal inclination of the sacrum, the intact lumbar spine must assume a curve that is known as the lumbar lordosis. The shape of lumbar lordosis is achieved as a result of several factors. One of the main factors is the shape of the lumbar discs, and particularly the L5-S1 lumbosacral intervertebral disc. The L5-S1 lumbosacral disc, more than other lumbar intervertebral discs, is substantially wedge-shaped. Typically, the posterior disc height is about 6 or 7 mm less than its anterior height. The angle formed between the bottom of the L5 vertebrae and the top of the sacrum (S1) is found to vary from person to person in a range of roughly 5 to 30 degrees, with an average value of about 16 degrees.

One important advantage that derives from the lumbar lordosis is resilience to compressive forces and shocks. In a straight lumbar spine, axial compressive forces would be transmitted through the vertebral bodies and intervertebral discs and the only mechanism to protect the lumbar vertebra would be the shock-absorbing capacity of the intervertebral discs.

In a normally curved lumbar spine, compressive forces are transmitted through the posterior ends of the intervertebral discs while the anterior ends of the vertebral bodies tend to separate. Compression tends to accentuate the lumbar lordosis, which tendency tenses the anterior ligaments, which in turn resists the accentuation. Thus some of the energy of the axial compressive force is diverted into the stretching of the associated ligaments instead of being transmitted directly to the next vertebral body. In order to restore relatively normal biomechanical relationships to the vertebral column having structural derangements severe enough to require prosthetic spinal disc implantation, the prosthesis ought to provide for and replicate—as much as possible—the normal lordosis found in the healthy spine.

Axial compression is the movement that occurs during weight-bearing in the upright posture, or as a result of contraction of the longitudinal back muscles. During compression, intervertebral discs undergo an initial period of rapid creep, deforming about 1.5 mm in the first 2 to 10 minutes depending on the size of the applied axial load. Subsequently, a much slower but definite creep continues at about 1 mm/hour. Depending on age, a plateau is attained by about 90 minutes beyond which no further creep occurs. It is therefore important to incorporate this gradual accommodating compression—this cushioning—of the intervertebral disc to axial loads as part of the effort to restore and replicate normal vertebral biomechanics as much as possible.

During the axial rotation of an intervertebral joint inherent in twisting movements, the normal intervertebral disc resists torsion more than bending. Normally, the stress-strain curves for torsion rise steeply in the range of 0 to 3 degrees of rotation; beyond 3 degrees very large forces have to be applied to rotate the disc further. The risk of disc element failure increases substantially as the amount of rotation approaches 12 degrees, suggesting that 12 degrees is normally the maximal range of rotation. Thus, in order to replicate normal spine movements, an implanted prosthetic spinal disc ought to permit at least 3 degrees of rotation and preferably between 8 and 12 degrees of maximal rotation. None of the currently available disc prostheses provide for anything close to this amount of rotation.

Commonly used implantable spinal prosthetic devices include semi-rigid elastomeric filler materials that are sandwiched between two layers of some bio-compatible metal. The upper and lower plate surfaces typically have multiple spikes for their fixation to the vertebral end plates. Other similar devices offer means to screw the upper and lower plates to the co-joining vertebrae and some also include plates treated to promote bone growth into them. A few of the newer devices permit a small amount of articulation between the vertebrae but the extent of flexing and twisting is quite limited; furthermore, the elastomeric materials and their bonding agents in these devices have a disappointingly limited longevity. Ideally, a spinal disc prosthesis should last 30 to 40 years and be able to withstand approximately two million compression cycles per year.

It is a purpose of this subject invention to provide an implantable spinal disc prosthesis assembly comprising a combination of selectable modular components that has a long life expectancy, a negligible rate of failure and/or complications, and provides for maximal articulation in all normal physiological planes of movement within the spine. More particularly, the subject spinal disc prosthesis allows for tilting from side-to-side, rotation such as with twisting movements, and compression along a primary axial direction to absorb and transmit axial loads typical for normal activities.

PRIOR ART

Among the prior art spinal prosthesis is the device in U.S. Pat. No. 5,002,576. The patent reference is directed to an intervertebral disc prosthesis. This reference teaches a prosthetic disc device provided with a central elastomeric layer sandwiched between two cover plates. This particular prosthetic disc device offers neither rotation between the vertebra nor does it provide for any significant amount of bending in the forward, backward, or side directions.

Another prior art prosthetic disc implant is shown in U.S. Pat. No. 4,932,975. This reference patent is directed to a vertebral prosthesis. The prosthetic device disclosed in this patent includes a flexible bellows but the bellows here do not allow for rotation between the two adjacent vertebrae.

U.S. Pat. No. 3,875,595 discloses and claims intervertebral disc prosthesis along with instruments for positioning the same. The prosthesis is a hollow, bladder-like member with an expanded shape having the appearance of a natural nucleus of a normal spinal disc. The device does not provide for rotation between adjacent vertebrae, thus failing to provide the patient will full articulated movement.

U.S. Pat. No. 5,571,189 is directed to an expandable fabric implant for stabilizing a spinal motion segment. The implant is in the form of an inflatable bag positioned within a cavity artificially formed intervertebrally within the spine. The inflatable bag does not allow for rotation of that spinal motion segment.

Yet another prior art prosthesis is disclosed in U.S. Pat. No. 5,755,807. This patent is directed to an implant module unit and rotating seal for a prosthetic joint. The implant includes a ball-and-socket joint surrounded by a flexible metallic bellows. The system has certain limitations, namely, that it is subject to wear and premature failure as a result of friction and the buildup of particle debris.

U.S. Pat. No. 5,401,269 discloses an intervertebral disc prosthesis, the Charite' disc prosthesis. This prosthesis does allow some minimal rotational movement, as well as a small amount of tilting and bending movement, by providing for an articular surface with surface forms curved with different average radii in the median section and the frontal section. Unlike the present invention, the Charit prosthesis does not provide for axial compression. In addition, the Charit prosthesis allows for some translational movements, which while mimicking normal physiological movements to some extent may not be well tolerated in the context of the multi-level spine degeneration typical of patients requiring such prosthetic implants. Furthermore, the components of the Charit prosthesis do not allow for individualization of the device's axial load-bearing capability; in contradistinction to the present invention, Charit prostheses offer negligible shock absorption and seems to permit progression of the Transition Syndrome whereby spinal levels above and below the implanted level suffer progressive disc and joint degeneration.

The present subject application device provides for improvements to the rotatable, compressible and tilting functions of the parent application device. The crown plate members as disclosed and claimed herein inventively provide for both selectable lordosis angles and selectable cross-sectional profiles. The selectable rotatable, compressible and tiltable cartridges have pre-loaded bellows that extend the device's functional lifetime indefinitely. The cartridges also provide enhanced axial load-bearing and shear-resisting capabilities as a result of the axial load bearing mechanism comprised of biasing members—a dashpot and springs in the preferred embodiment—positioned within the cartridge's bellows assembly. The selectable modular components of the present spinal disc prosthesis assembly permit optimization of the disc prosthesis assembly on a patient-by-patient basis.

The prior art does not include a combination of elements forming a modular compressible, rotatable and tiltable spinal hydraulic prosthesis assembly that is optimizable on a patient-by-patient basis. The present invention solves the problematic unavailability in the prior art of individually optimizable spinal disc prostheses by providing for crown plates selectable according to a best cross-sectional profile and lordosis angle, where selected crown plates are best for a particular patient's needs; and for selectable cartridges with pre-loaded metallic bellows having redundant biasing elements to augment axial load-bearing and shear-resistance. The selectability of a spinal prosthesis components—as provided by the present invention—according to selectable lordosis angles, selectable crown plate shapes and sizes, and selectable load-bearing capabilities, permits optimization of the spinal disc implant assembly that is tailored to an individual patient. Optimization is accomplished by selecting the specific disc prosthesis components according to important relevant factors that may include the particular patient's gender, age and body habitus, the extent of co-existing spinal degeneration at nearby spinal levels, the patient's level of activity and general condition, as well as the particular spinal level(s) in need of prosthetic spinal disc replacement.

SUMMARY OF THE INVENTION

The present invention provides for a compressible, rotatable, and tiltable hydraulic spinal disc prosthesis system with selectable modular components. The system comprises an individually optimizable compressible, rotatable, and tiltable hydraulic spinal disc prosthesis assembly for the surgical replacement of a severely diseased or missing intervertebral disc, as well as at least one insertion instrument to facilitate the surgical implantation of this hydraulic disc prosthesis assembly.

The present modular hydraulic spinal disc prosthesis assembly further provides for selectable crown plate modules that sandwich between them at least one selectable compressible, rotatable and tiltable hydraulic disc prosthesis cartridge, the crown plates being affixed to the corresponding opposed vertebral end plates.

The selectable cartridge interposed between the crown plate modules is comprised of pre-loaded flexible bellows preferably capped at the cephalad end of the bellows by a center bearings plate, and at the caudal end by an endcap having formed therein a sealable fluid conduit to facilitate filling and pressurizing the bellows and dashpot chambers with a mixture of compressible and non-compressible fluids.

The rotational elements are preferentially ceramic components slidingly juxtaposed and lubricated by water or the like, thereby providing for substantially normal articulated rotational movement at that spinal motion segment. The cartridge bellows assembly is hermetically sealed at the ends to provide a fluid-tight chamber containing an axial load-bearing mechanism. The axial loads are absorbed, transmitted and dispersed by a combination of a dash pot located centrally in the bellows assembly, and at least one biasing member such as a coil spring in close proximity to the dashpot to augment the axial load bearing capability provided by the bellows assembly and the dashpot. The selectable nature of the spring and load bearing elements allows the optimal choice among selectable cartridges to best accommodate anticipated demands as presented by particular clinical situations. Furthermore, the dashpot piston is provided with a spherical ball bearing—preferably made of a ceramic material or the like—through which the piston extends, which ball bearing is constrained by a shear-resisting retainer ring seated within the bellows assembly.

Additionally, the lifespan of the bellows element, which is subjected to repeated axial loading and unloading under a spectrum of tilting and bending movements, is extended indefinitely by preloading the bellows to a sub-atmospheric pressure as described herein.

It is a principle objective of the subject invention to provide a hydraulic spinal prosthesis for replacement of a missing or diseased intervertebral spinal disc and annulus.

It is a further objective of the subject hydraulic spinal prosthetic device to provide a hydraulic spinal prosthesis with dimensions and load-bearing capabilities that can be optimized for individual patients.

It is yet a further objective of the subject hydraulic spinal prosthesis device to provide a spinal disc replacement that permits substantially physiologic range of motion—including rotation—between the vertebrae adjacent to the implanted prosthesis.

It is also an objective of the subject inventive concept to provide a hydraulic spinal prosthetic device that resists translation and shear movements in the horizontal, coronal and sagittal planes.

It is also an important objective of the present invention to provide a hydraulic spinal prosthetic device provided with a selectable cartridge having a set of bellows filled with a mixture of compressible and incompressible fluids and preloaded to a sub-atmospheric pressure so as to very substantially prolong the functional lifespan of the implanted hydraulic spinal disc prosthesis.

It is yet another objective of the present invention to provide a hydraulic spinal prosthetic device having selectable load bearing capability afforded through the bellows, the dash pot mechanism, as well as by at least one further biasing member, such as coil spring(s).

It is a further important objective of the present invention to provide a hydraulic spinal prosthesis with fluid-filled bellows that have a washer-convoluted design, and which permits a substantially physiologic range of movements.

An important objective of the present inventive device is to provide a prosthetic hydraulic spinal disc replacement that reduces the incidence of Transition Syndrome.

The present inventive device takes as an important objective to provide a hydraulic prosthetic spinal disc replacement that does not migrate from its initial implantation position.

It is an important objective of the present inventive device to provide a hydraulic prosthetic spinal disc replacement that improves the patient's spinal stability at the affected motion segment as well as at nearby spinal levels.

It is a further objective of the present invention to provide a modular hydraulic spinal prosthesis device and corresponding insertion instrument(s) that does not demand unusual or extraordinary surgical skills to implant an individually-optimized spinal prosthesis assembly properly. The terms "insertion instrument" and "insertion tool" are used interchangeably and synonymously throughout the disclosure.

BRIEF DESCRIPTION OF THE DRAWINGS

FIG. 1B is a perspective view of the insertion tool coupled with the hydraulic spinal disc prosthesis assembly;

FIG. 1C is a cross-sectional view through line 1C-1C in FIG. 1B showing the mechanical coupling of the insertion tool with the spinal disc prosthesis assembly;

FIG. 4A is a cross-sectional elevational view of the hydraulic spinal disc prosthesis assembly through the line 4A-4A in FIG. 4C;

FIG. 4B is a left lateral side-view of the hydraulic spinal disc prosthesis assembly;

FIG. 4C is a posterior—anterior side-view of the hydraulic spinal disc prosthesis assembly;

FIGS. 5A and 5B are lateral side-views of the crown plates and bellows cartridge respectively, illustrating their assembly;

FIG. 5C is a rear posterior—anterior side view of the top crown plate member;

DESCRIPTION OF THE PREFERRED EMBODIMENTS

Figure 1A:
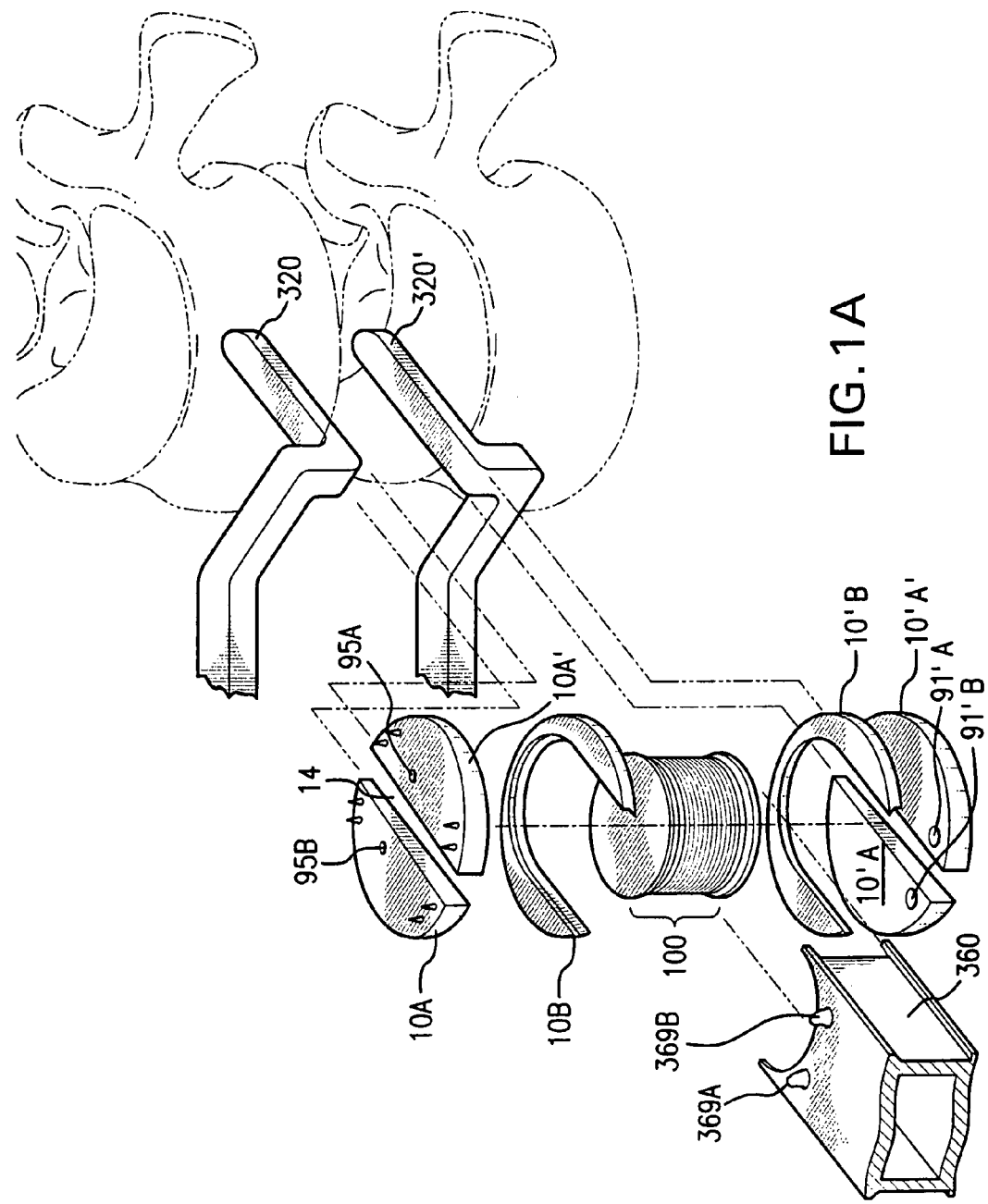
FIG. 1A is an exploded perspective view of the hydraulic spinal disc prosthesis system.
Figure 2:
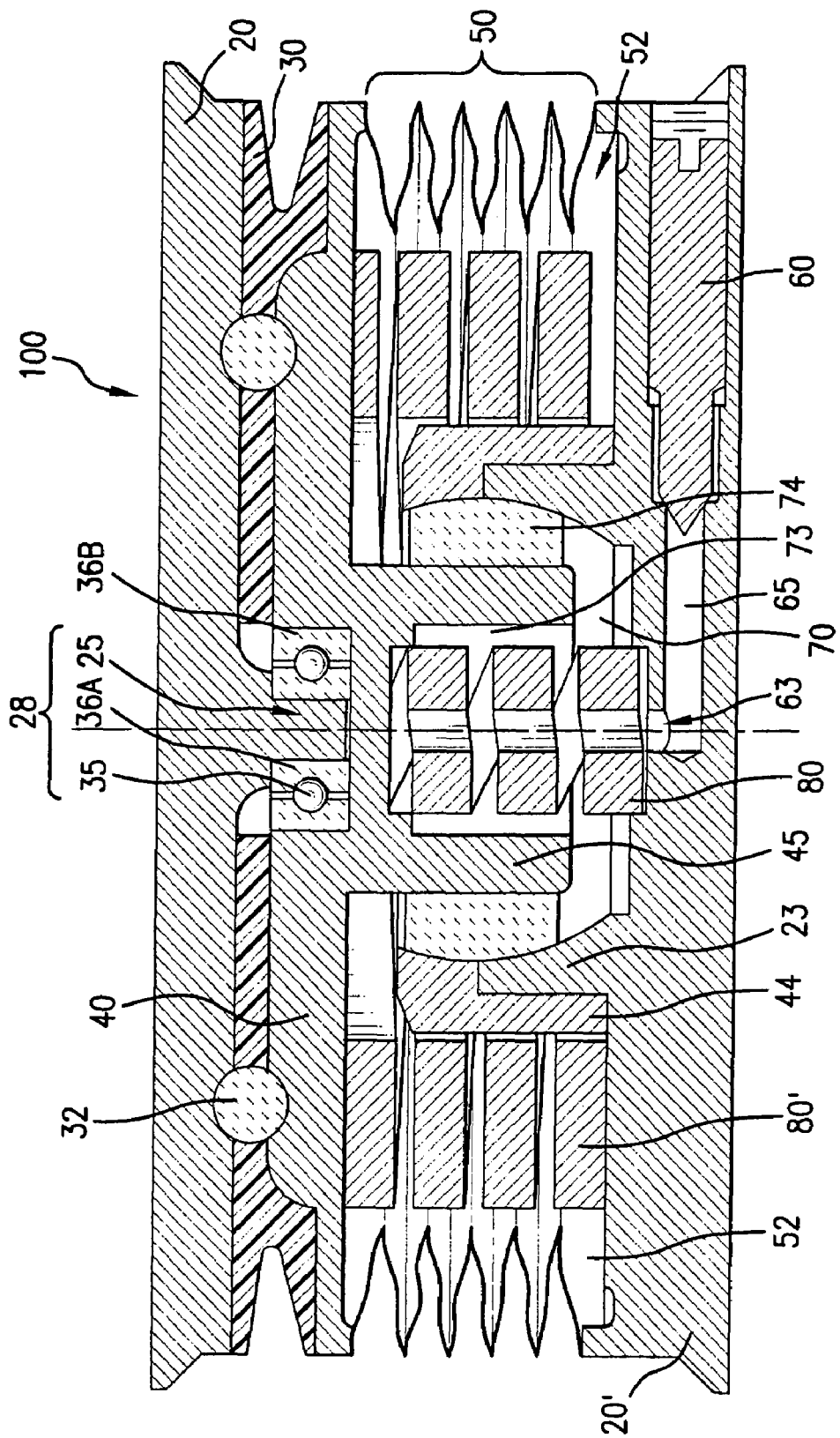
FIG. 2 is a cross-sectional view of an alternative preferred embodiment of the bellows cartridge of the hydraulic spinal disc prosthesis assembly.

Referring now to the figures, there is shown a compressible, rotatable, and tiltable hydraulic spinal disc prosthesis system with selectable modular components. As seen in FIG. 1A. Prosthetic modular assembly 1 includes an opposed pair of crown plate modules 10A and 10B, 10A' with 10B and 10'A and 10'B, 10'A' with 10'B which make up crown plates 10 and 10' respectively, and a bellows cartridge 100 sandwiched between the crown plates 10 and 10' (seen in FIG. 4C). The bellows cartridge 100 as seen in FIG. 2 is comprised of a cephalad end cap member 20, a caudal end cap member 20', and an assembly of compressible, rotatable and tiltable bellows assembly 50 between them.

The bellows assembly 50 is rotatably coupled at the cephalad end to the cephalad end cap member 20 by at least two sets of ball-bearings 35, 32. The first rotatable coupling is a radial thrust bearing assembly 28 comprising a first race 36A and B and ball bearings 35 and positioned to resist shearing forces. Axial rotation is further supported by a second bearing assembly with a plurality of ball-bearings 32 maintained in regular spacing in a respective race by a bearing retainer seal member 30 interposed between the cephalad end cap member 20 and the center bearings plate 40. The second race, in which the ball-bearings 32 travel, is formed at its the top and bottom by a pair of opposed annular recesses defined in the opposing surfaces of the cephalad end cap member 20 and the center bearings plate 40, and laterally by the arcuate edges formed in the retainer seal 30. The second bearing assembly is positioned to rotationally transmit axial loads placed on the system. The two races are offset longitudinally relative to each other, adding to the system's stability and resistance to shearing forces.

The caudal end, or synonymously, inferior endcap of the bellows cartridge 100 is fixedly attached to the caudal crown plate 10'. The caudal end cap member 20' of FIG. 3A has formed therethrough a fluid channel 65 in fluidic communication with the fluid-filled bellows chamber 52 by means of aperture 67, and in further fluid communication with the dashpot chamber 70—by means of opening 63. Seen within the bellows assembly 50 is the dashpot mechanism comprising a piston 45 formed from the center bearings plate 40 as a cylindrical protrusion received into the dashpot chamber 70 which is defined by extensions of the caudal end cap member 20' at the other end to the cephalad end cap member and a retaining ring 44 defining the cephalad limit of the dashpot chamber 70.

Fixedly juxtaposed onto those end cap extensions, the interior wall of the retaining ring 44 in the preferred embodiment, assumes the shape of a sphere with a substantial flattening of the opposing poles of the sphere and defining a cylindrical shape for its outer surface. The retaining ring 44 is juxtaposed with the bearing 74 which assumes the shape of a cored sphere defining a cylindrical shape for its inner surface, and likewise, the dashpot piston 45 is slidably mounted through the bearing 74, so that the dashpot piston 45, the bearing 74, and the retaining ring 44 are all coaxial with the bellows assembly 50. As in FIG. 2, at least one biasing mechanism 80, 80' is incorporated within the bellows assembly 50 and, in a preferred embodiment, is coil spring 80 positioned within recess 73 formed centrally within the dashpot piston 45. In the preferred embodiment illustrated in FIG. 2, coil spring 80 extends in a caudal direction to be received into recess 73 formed centrally within dash pot piston 45, which in this embodiment protrudes caudally from center bearings plate 40.

Referring to FIG. 4C, crown plate 10 is seen in cross-sectional side view demonstrating certain of its important component elements. The crown plates 10, 10' are formed by the joining of two vertebral engaging lordosis half-plates 10A, 10A' onto U-shaped cartridge engaging plate 10B; in the preferred embodiment the two half-plates 10A, 10A' are machined separately and then spot welded to 10B thereby forming a unitary crown plate 10. As seen in FIG. 4A, the inner surface of the U-shaped cartridge engaging plate 10'B has two substantially parallel straight edges 7 that are continuous with a substantially circularly shaped edge 6 connecting the straight edges 7 at the posterior aspect. Both the straight and circular sections of the inner edge of cartridge engaging plate 10'B are beveled or chined (as seen in FIG. 4C) to matingly receive the complementarily beveled or chined edges of the bellows cartridge end caps 20 respectively.

The selectable lordosis angle refers to the angle formed between the vertebral engaging surface of the crown plate top 10A and the bottom surface of crown plate 10B fixedly connected to the cephalad end cap 20 of bellows cartridge 100. The selectable crown plates 10, 10' have a cross sectional profile that may be further chosen so as to best match in size and shape the patient's vertebral end plate to which the prosthetic modular assembly 1 is to be fixedly attached.

Figure 3A:
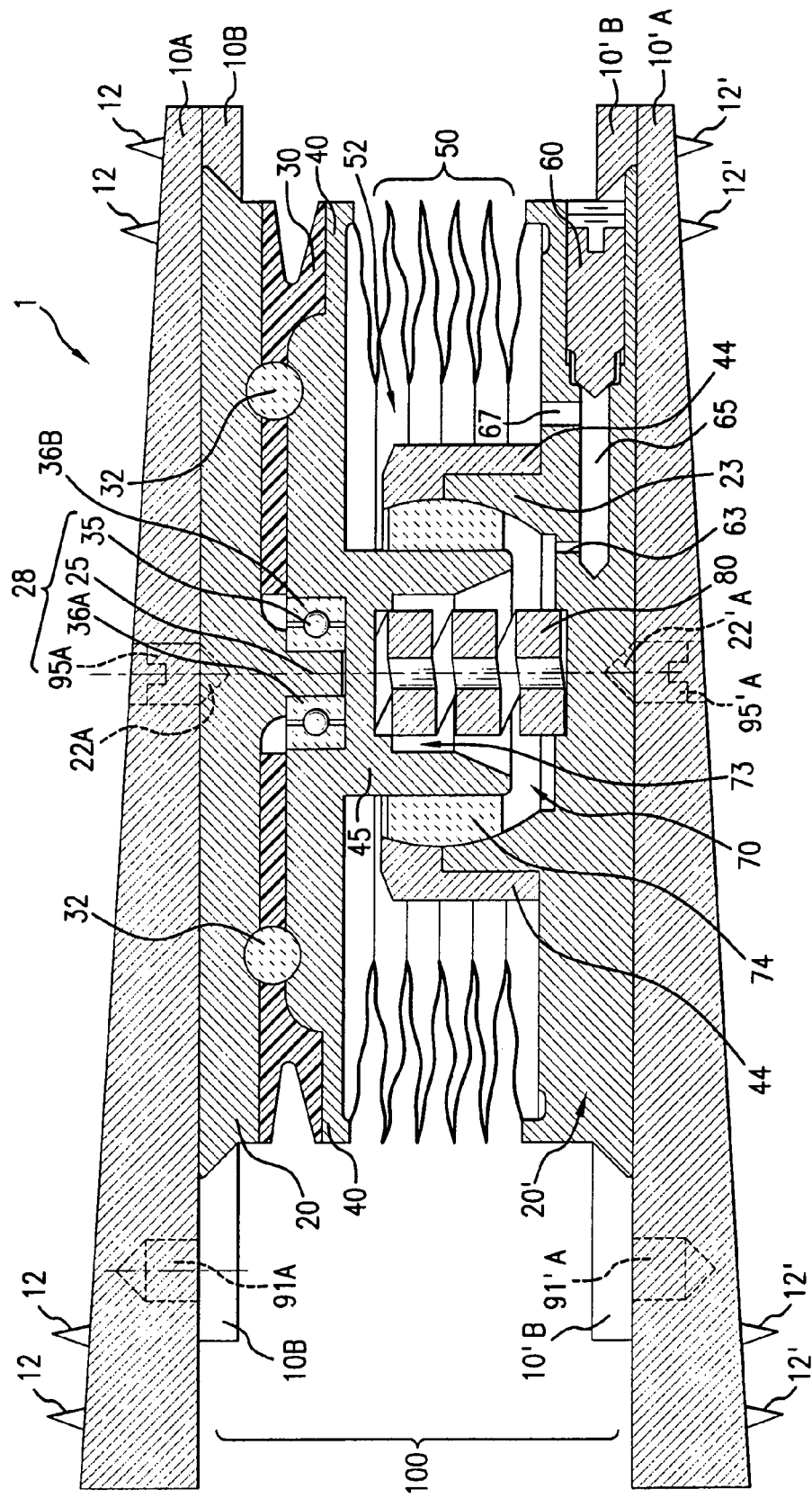
FIG. 3A is a cross-sectional view of a preferred embodiment of the hydraulic spinal disc prosthesis assembly in an untilted condition.
Figure 3B:
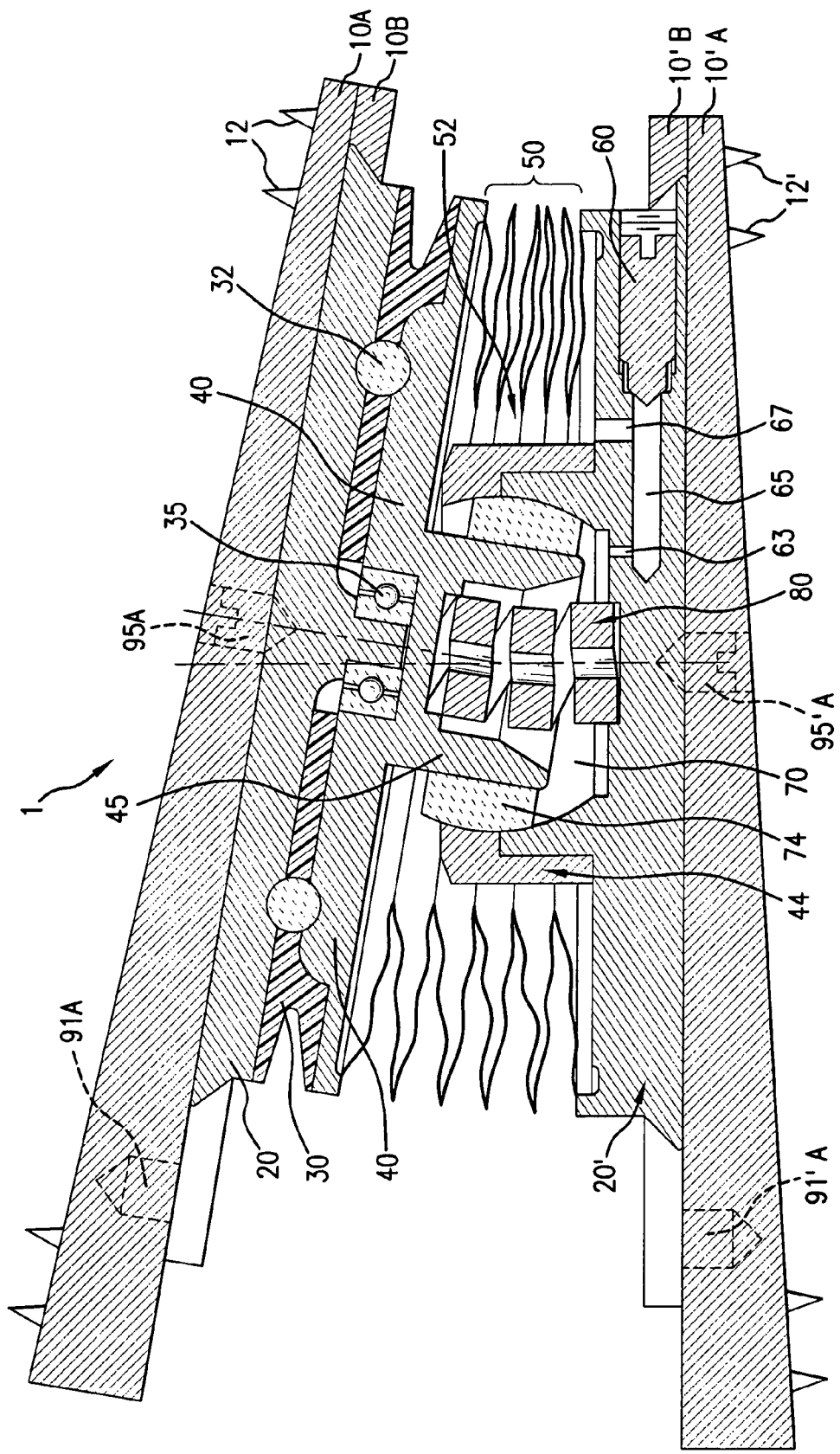
FIG. 3B is a cross-sectional view of a preferred embodiment of the hydraulic spinal disc prosthesis assembly in a tilted condition.

On the vertebral engaging surfaces of the crown plates 10 and 10' there are a plurality of spikes 12, 12' respectively, formed and protruding from the vertebral engaging crown plate surfaces at the periphery, and designed to secure the prosthetic modular assembly 1 in position between the adjacent vertebrae. In the preferred embodiment each vertebral engaging crown plate surface has six spikes 12, but the number of such spikes are preferably in the range of two to eight spikes. Further apparent from FIG. 4C is a pair of threaded through-holes 95A, 95B and 95'A, 95'B spaced equidistant from the device's center of axial rotation. In FIG. 5A, the pairs of threaded through-holes 95A and 95'A are positioned so as to align with a corresponding pair of set screw recesses 22A, 22'A formed on the top and bottom surfaces respectively of the bellows cartridge 100 (as seen in FIG. 3A, 3B) for receiving set screw pairs 96A, 96'A of FIG. 5A inserted therein for locking together cartridge 100 and crown plates 10, 10'.

Further evident in FIG. 1C are the paired opposing pawl recesses 91A, 91'A formed in the anterior aspect of opposed inner surfaces of crown plates modules 10A and 10'A and adapted to receive therein a securing element or pawl 369A, 369'A of insertion instrument 300 for purposes of intra-operative device placement. As may be further appreciated from the perspective views of the prosthetic modular assembly 1, as seen in FIG. 4C, a through channels 14, 14' are formed in the vertebral engaging surface of crown plate members 10 and 10', in between 10A and 10A'; and 10'A and 10'A' respectively. The through channels 14 are centrally located, extend between the anterior and posterior edges of the crown plate members 10 and 10' and, in the preferred embodiment, have a chined or beveled cross-sectional profile. The through channels 14 are important for the proper stereotactic positioning of the prosthetic device 1 during surgical implantation.

Additionally, the vertebral engaging surfaces of the crown plates 10, 10' are formed with a roughened irregular surface, having a sintered or otherwise textured surface so as to facilitate the permanent fixation of the prosthetic modular assembly 1 subsequent to surgical placement and implantation. The cross-sectional profile of the through channels 14 matingly complement the distraction bars 320 of insertion instrument 300 as seen in FIG. 1A, thereby permitting prosthetic modular assembly 1 to be slidingly advanced—preferably from anterior to posterior—along the previously positioned distraction bars 320 to a preferred position relative to the vertebrae and associated spinal structures. In the preferred embodiment, the through channels 14, 14' have parallel lengths, but tapering sides or other functionally equivalent shapes are within the contemplation and scope of this invention.

Figure 6A:
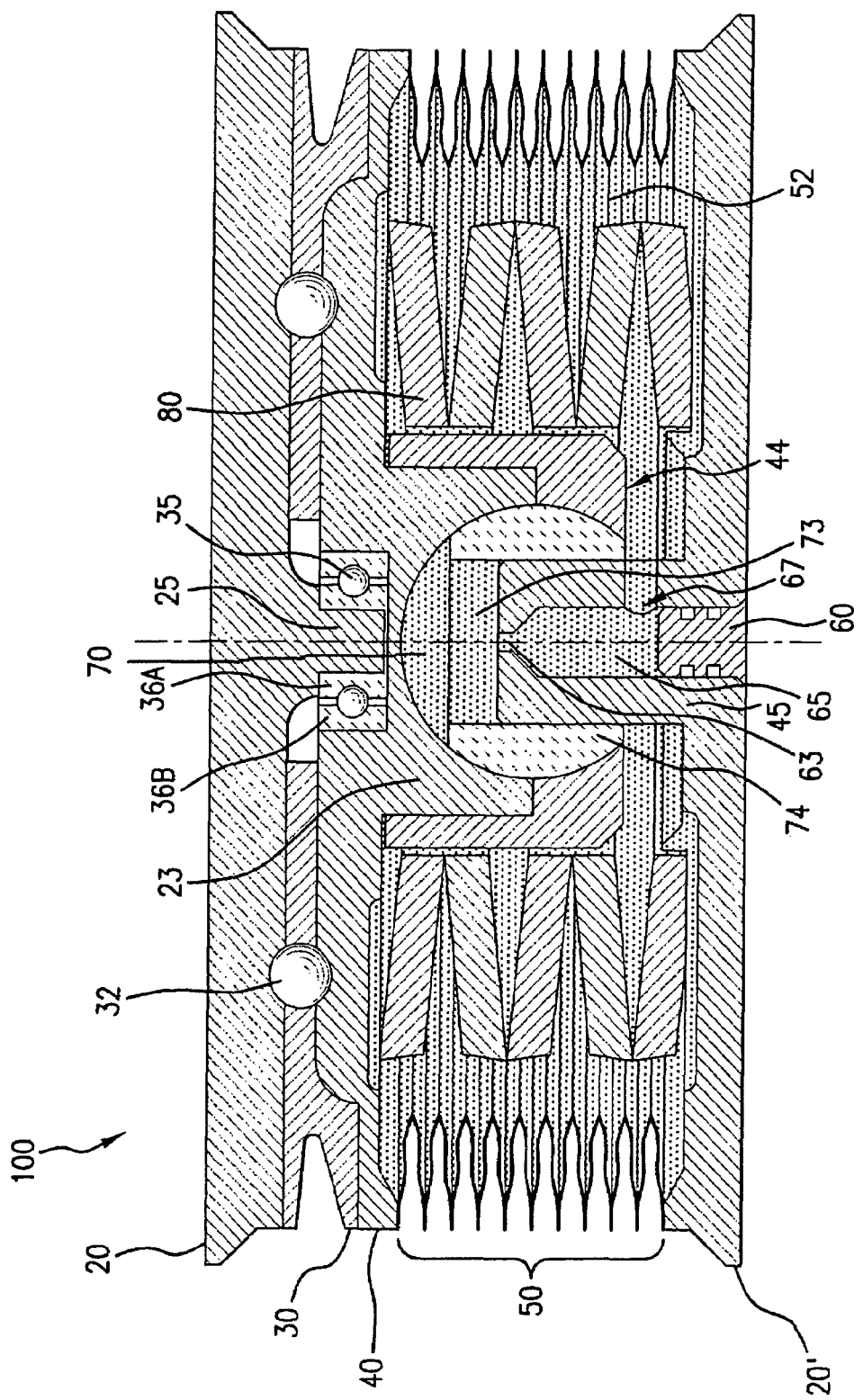
FIG. 6A is a cross-sectional view of the preferred embodiment of the bellows cartridge in an untilted condition.

As seen in FIG. 6A, the bellows cartridge 100 is comprised of a compressible and tiltable bellows assembly 50 that, together with center bearings plate 40 and caudal end cap 20' which cover the top and bottom bellows openings, define a bellows chamber 52. In another embodiment, the bellows assembly 50 is compression biased by a plurality of Belleville washers 80. The bellows assembly 50 is preferably comprised of titanium but other like materials are also contemplated. Bellows chamber 52 is filled with a mixture of compressible and non-compressible fluids and fluidically communicates with the dash pot chamber 70, 73 by fluid conduits 63, 65, and 67 as illustrated in FIGS. 2, 3A, 3B, 6A and 6B.

The 360° rotation afforded by the prosthetic modular assembly 1 is provided structurally by a bearing retainer ring 30 formed with regularly-spaced through-holes to accept a plurality of ball-bearings 32 rollably positioned between center bearings plate 40 and cephalad end cap 20. The ball-bearings 32 roll around in the race defined by the partly circular channels formed on opposing surfaces of center bearings plate 40 and end cap 20 respectively, with the bearing retainer seal member 30 maintaining the ball-bearings 32 in a preferred spacing. As may be seen in FIGS. 2, 3A, 3B, 6A and 6B, the arcuate lateral edges formed in the spaces of the bearing retaining seal member 30 further define the race in which the ball-bearings 32 make rotatable contact. In a preferred embodiment, the number of ball bearings 32 is in a range of 6 to 12.

Additionally, in FIGS. 2 and 3A, a radial thrust bearing assembly 28 is centrally placed in the bellows cartridge 100 and comprises a caudal cylindrical protrusion 25 formed from and extending down from cephalad end cap 20; inner and outer encircling race members 36A, 36B; and a plurality of ball bearings 35 rotatably seated in the race formed by the opposing inner and outer race members 36A, 36B respectively. This axially formed caudal cylindrical protrusion 25 is received in a cephalad recess of the center bearings plate 40 and is positioned coaxial with the axis of rotation of the bellows cartridge 100. Inner encircling race member 36A is fixedly coupled with the caudal cylindrical protrusion 25 of end cap 20, and outer encircling race member 36B is fixedly positioned within the centrally positioned cephalad recess of center bearings plate 40.

The dashpot mechanism is coaxial with and centrally positioned within the bellows assembly 50 and comprises a central axial dashpot piston 45 formed from an inner horizontal surface, which dashpot piston 45 has formed within it a fluid-filled recess 73 that is a fluidic extension of dashpot chamber 70. The dashpot piston 45 is slip fitted in and through the central axial bore of spherical bearing 74; preferably, spherical bearing 74 is formed with the shape of a cored sphere. The substantially spherical lateral sides are in sliding juxtaposition with the dashpot walls. In the preferred embodiment both the spherical bearing 74 and the retaining ring 44 are composed of a ceramic material—for which water or similar aqueous solutions are an excellent lubricant. The use of $Si_3N_4$ or other similar ceramics such as $Al_2O_3$, or like materials, for the spherical bearing 74 as well as ball bearings 32, 35, is within the contemplation and scope of the subject inventive concept.

At least one biasing member, which in the preferred embodiment is a coil spring member 80, is coaxially mounted within and/or around dashpot piston 45 as seen in FIGS. 2, 3A, 3B, 6A, 6B and 7. The coil spring represents a preferred embodiment of biasing members that can be used to augment the load-bearing capabilities of the prosthetic modular assembly 1. Different types of springs, as well as different spring constants for the chosen springs, allow for selectability of the bellows cartridge 100 according to the needs of a particular patient. Without intending to be bound by particular examples, the spring rate for cervical implantation of the prosthetic modular assembly 1 is typically about 375 pounds per square inch; for lumbar implantations the spring rate is typically about 575 pounds per square inch.

In FIG. 3A, the caudal end cap 20' has formed within it a fluid channel 65 that fluidly connects the dashpot chamber 70, the bellows chamber 52 and an internal aperture 67. Channel 65 is adapted to receive a sealing plug or screw 60 that creates a watertight closed chamber 65, 70, 73, and 52 when in place. The dashpot chamber 70 communicates with the fluid channel 65 by means of aperture 63; the bellows chamber 52 is in fluidic communication with the fluid channel 65 by means of opening 67. By suitable factory adjustment and design selection of the diameter(s) of aperture 63 and/or opening 67, the dampening function of the dashpot may be adapted to control how rapidly fluid can flow through those apertures during a down stroke of the piston 45, and then during the subsequent recovery upstroke of the piston 45.

The bellows chamber 52 and the dashpot chamber 70 that are fluidly connected by the fluid channels 63, 65 and 67 as discussed above, contain a mixture of compressible and non-compressible fluids so as to resist axial loads while providing some cushioning or yielding to those axial loads. It has been found that the functional life span of the device is substantially extended when the bellows chamber 52 is preloaded with fluid at a sub-atmospheric pressure. Preloading the bellows chamber 52 to a predetermined sub-atmospheric pressure is important and preferred for the present subject hydraulic spinal disc prosthesis assembly.

The method of preloading the compressible, rotatable and tiltable bellows cartridge 100 is accomplished by first providing a compressible, tiltable bellows assembly 50 and then compressing the biasing member(s) 80 to solid height—which is to say to the full stroke excursion-typically in the range of 0.05 to 0.06 inches. This compressed condition of bellows cartridge 100 is maintained by applying a constraining member (such as a clamp or the like) to the compressed bellows cartridge 100. Subsequently, the compressed bellows cartridge 100 with the fluid channel 65 unplugged is placed into a vacuum chamber and the air is evacuated down to about 17-18 Torr at 20° C. while the compressed cartridge 100 is fully immersed in a fill fluid. While immersed, the cartridge 100 is exposed to sub-atmospheric pressure in the vacuum chamber so as to evacuate substantially all the air from the inside of bellows chamber 52, dashpot chamber 70 and the associated fluid conduits 63, 65, 67. Once this has been accomplished, the pressure in the vacuum chamber is adjusted back to atmospheric pressure which causes the immersed bellows assembly 50 to fill with the fluid. At this point the cartridge 100 with its compressed bellows assembly 50, now filled with the fluid, is taken out of the vacuum chamber and fluid conduit 65 is sealed with the sealing member 60 such as a plug or screw or similar sort of elements.

Once the fluid conduit 65 is sealed, thereby closing the cartridge's bellows chamber 52 and dashpot chamber 70, the cartridge 100 is allowed to re-expand by removing any constraining member such as a clamp or the like, thereby permitting the biasing member(s) 80—such as the coil spring in proximity with the dashpot piston 45—to force apart the opposing end caps 20 and 20' and connected structures with approximately 250 to 325 pounds of compressed spring force for a lumbar prosthesis, thereby re-expanding the bellows cartridge 100 to its uncompressed condition.

The biasing member 80 within the cartridge 100 exerts a distracting force, preferably in the range of 250 to 325 pounds for a lumbar prosthesis that tends to separate the end caps 20 and 20' and connected structures. By uncompressing the bellows cartridge 100 containing the fluid that had been introduced at standard temperature and pressure, the bellows and dashpot chambers internal volumes, 52 and 70 respectively, expand. With the bellows cartridge 100 in the expanded condition, the fluid mixture occupies a proportionately larger volume thereby causing a concomitant lowering of pressure therein to sub-atmospheric levels; this accomplishes the pre-loading of the cartridge 100 by providing a sub-atmospheric fluid pressure within the fluid compartments of uncompressed bellows cartridge 100.

Figure 1D:
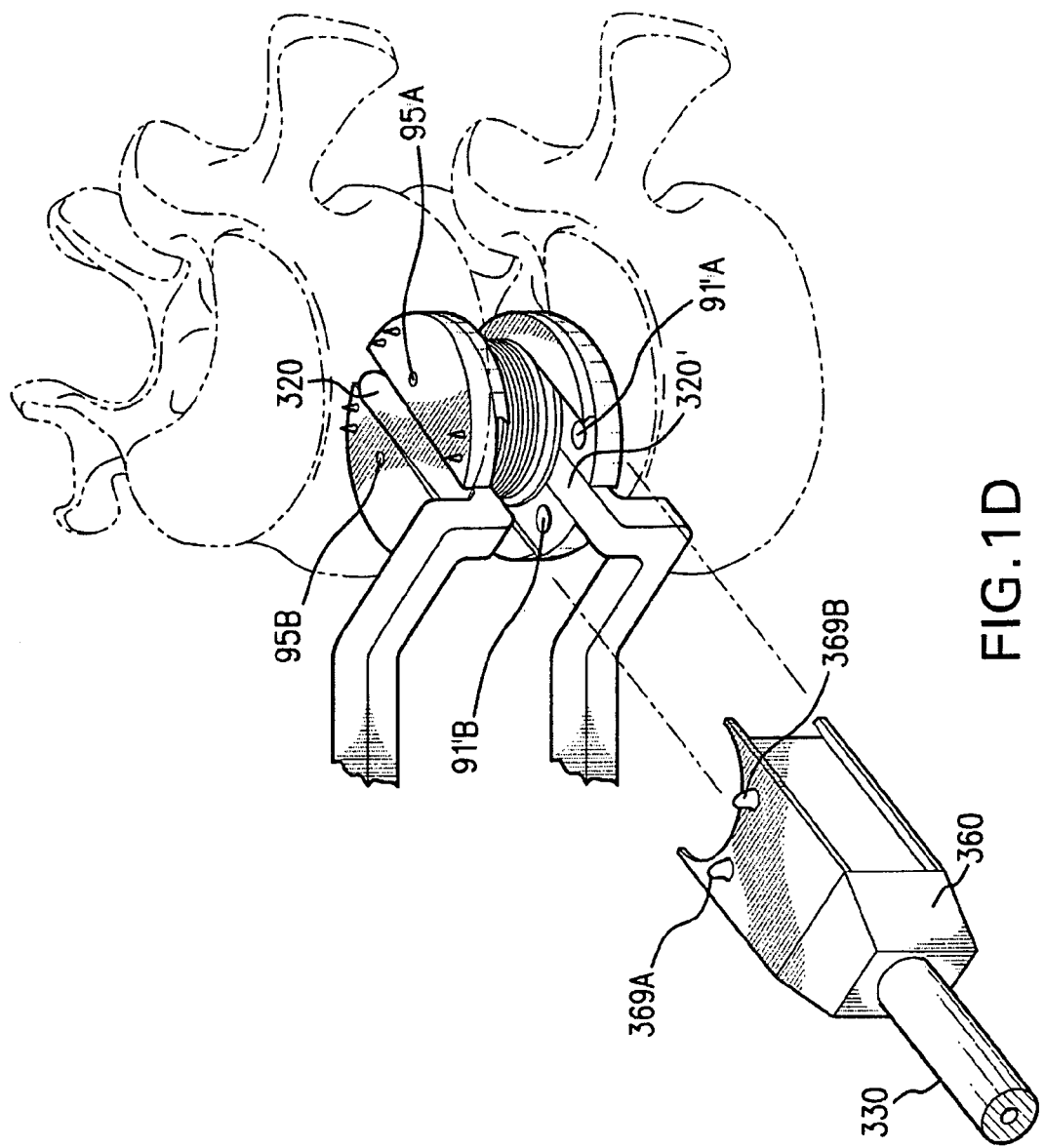
FIG. 1D is an exploded perspective view of the insertion instrument and the spinal disc prosthesis assembly in situ.

Per FIG. 1B, the insertion tool assembly 300 comprises a handle assembly 310 formed proximally at one end, and at the opposite end, the distal end, by a prosthesis engaging effector head 360; the handle assembly 310 further comprises an elongate tubular member 330 connecting the prosthesis engaging effector head 360 to handle grip member 340 and knob control mechanism 350. As illustrated in FIG. 4A, the proximal surface of the prosthesis engaging effector head 360 has a circularly arcuate profile with substantially the same radius of curvature as the circularly arcuate profile 6 of crown module 10B, 10'B and opposing end caps 20, 20' of the prosthetic modular assembly 1. Furthermore, the upper and lower edges of this proximal arcuate surface have chined or beveled contours that matingly complement the beveled or chined profile of the disc prosthesis cartridge end caps 20, 20'. Illustrated in FIG. 5A, are the set screws 96A, 96'A by which the cartridge 100 is fixedly secured to the respective crown plates 10, 10'. Pawl openings 91'A, 91'B of FIG. 1A, 1C, 1D, and 91A and 91'A of FIG. 4B and particularly 4A and 5A are respectively symmetrically placed lateral to through channel 14 and 14', and are aligned with the paired pawls 369A, 369B and pair 369' (as seen in FIGS. 1C and 1D) of the insertion instrument 300. When the insertion instrument 300 is slidingly juxtaposed with the chined upper and lower surfaces of cartridge 100, and pairs of pawl openings 91 and 91' respectively receive therein the pairs of pawls 369 and 369' so as to reversibly connect the insertion instrument 300 to the prosthetic modular assembly 1.

Per FIG. 1B, the insertion tool handle 340 has at its proximal end a threaded knob 350 that is axially rotatable. By rotating the threaded knob 350, a connecting rod 355 is displaced longitudinally either forward or backward according to the direction in which the threaded knob 350 is turned. By rotating the threaded knob 350 so as to thereby move connecting rod 355 proximally—which is to say away from the effector head 360—the distal end of the connecting rod 355, formed with at least one cam member 356 at its distal end, withdraws from pushing against at least one pair of hinged and spring-biased pawl-displacing lever arm members 370, 370'. As may be further appreciated by viewing FIG. 1C, withdrawing the connecting rod 355 displaces tapered cam member 356 away from the lever arms 370 and thereby allows biasing member 380 to push the pairs of pawls 369A, B and 369' (as in FIGS. 1C, 1D, and particularly 4A) into pairs of upper and lower pawl recesses 91 respectively. The reversible engagement of the pawls 369 with the respective recesses 91 effects a reversible connecting capture of prosthetic modular assembly 1 by the insertion tool 300; the assembled system as shown in FIG. 1B permits the surgeon to insert and position the prosthesis modular assembly 1 given the usual operative exposure.

As seen in FIG. 1C, the distal part of the insertion tool 360 has a height substantially equal to the height of the spinal disc prosthesis cartridge 100. Further illustrated in FIG. 4A is the profile of the crown plate 10'B, having a substantially U-shaped inner profile provided with beveled or chined edges that matingly complement the corresponding beveling of the prosthesis end caps 20. While the preferred embodiment shows the biasing member 380 tending to displace the pawls 369 apart, other arrangements are within the contemplation and scope of this invention, including biasing members 380 tending to pull the pawls 369 together.

Per FIGS. 1A and 1D, the insertion tool 300 further comprises a pair of distraction bars 320 whose dimensions matingly complement the through channels 14 so that distraction bars 320 act as guide rails for the prosthetic modular assembly 1 to be slidingly advanced into position along the distraction bars 320 during the implantation procedure.

As shown in FIGS. 2, 3A, 3B, 6A, and 6B, the retaining ring 44 is fixedly fitted onto the axial protrusion that surrounds piston 45, in sliding juxtaposition with the spherical dashpot bearing 74.

Figure 6B:
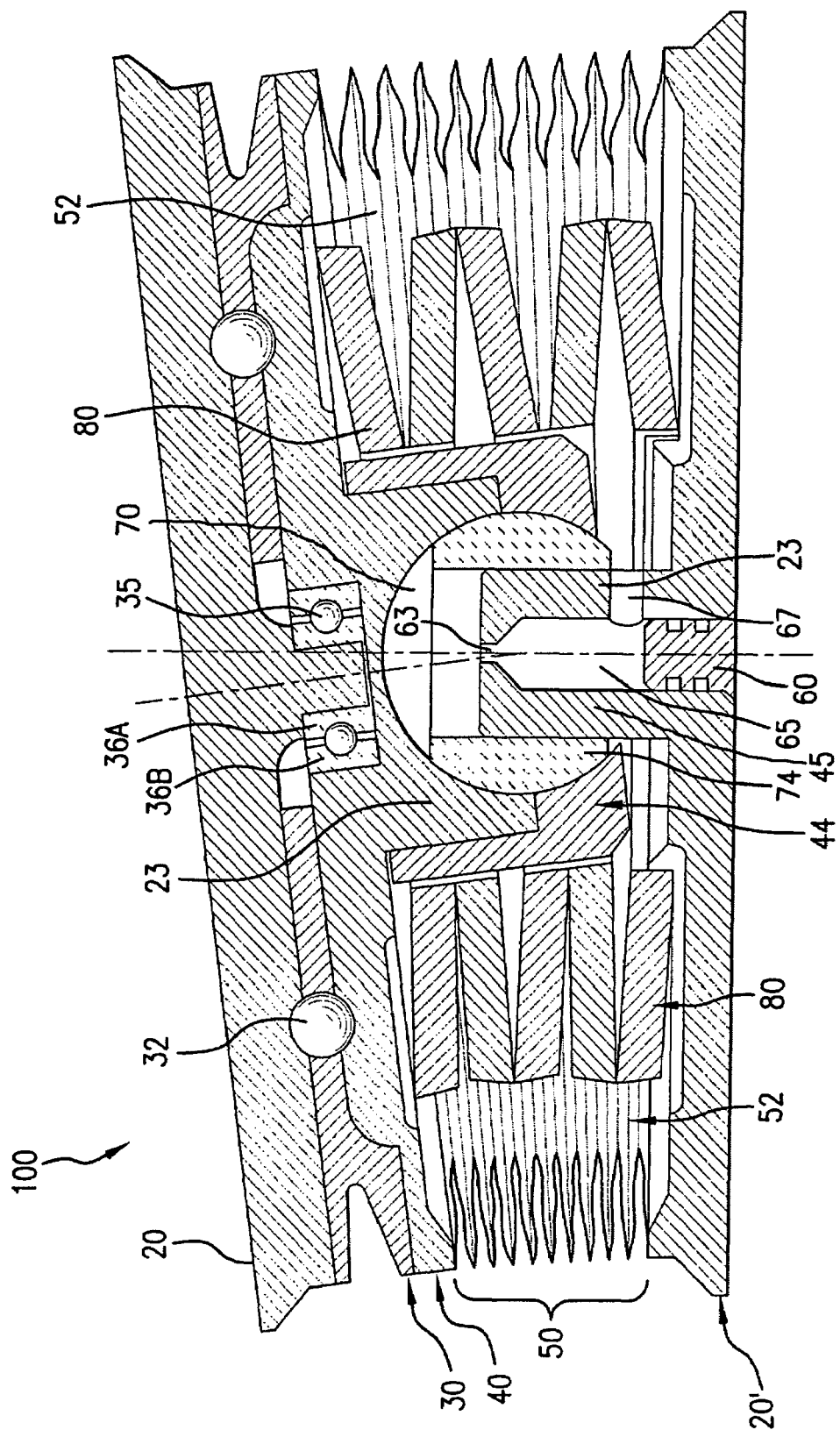
FIG. 6B is a cross-sectional view of the preferred embodiment of the bellows cartridge in a tilted condition.

FIGS. 6A and 6B show an alternative embodiment of the subject hydraulic spinal disc prosthesis, having the filling port positioned on the caudal surface of endcap 20' of the bellows cartridge 100. In this alternative embodiment, as axial forces cause compression of the disc assembly and concomitant downward movement of the dashpot elements, the spherical bearing 74 comes to completely occlude the bellows chamber opening 67 formed through the cephalad protrusion of the caudal end cap 20', thereby impeding fluid flowing from the dashpot chamber recess 73 formed in the caudal protrusion 23 of center bearings plate 40, as seen in FIGS. 6A and 6B, into the bellows chamber 52 through conduits 63, 65, and 67.

By variably impeding the equilibrating flow of fluid from the dashpot chamber recess 73 to the bellows chamber 52, the dashpot offers greater resistance to the imposed axial load than if unimpeded equilibration of the fluid pressure were permitted. Keeping constant all the other fluid conduit specifications, the total cross-sectional area of the bellows chamber openings 63 and 67 is the primary determinant of the impeded fluid equilibration that augments the device's resistance to axial forces, rather than the actual number of such openings.

Figure 7:
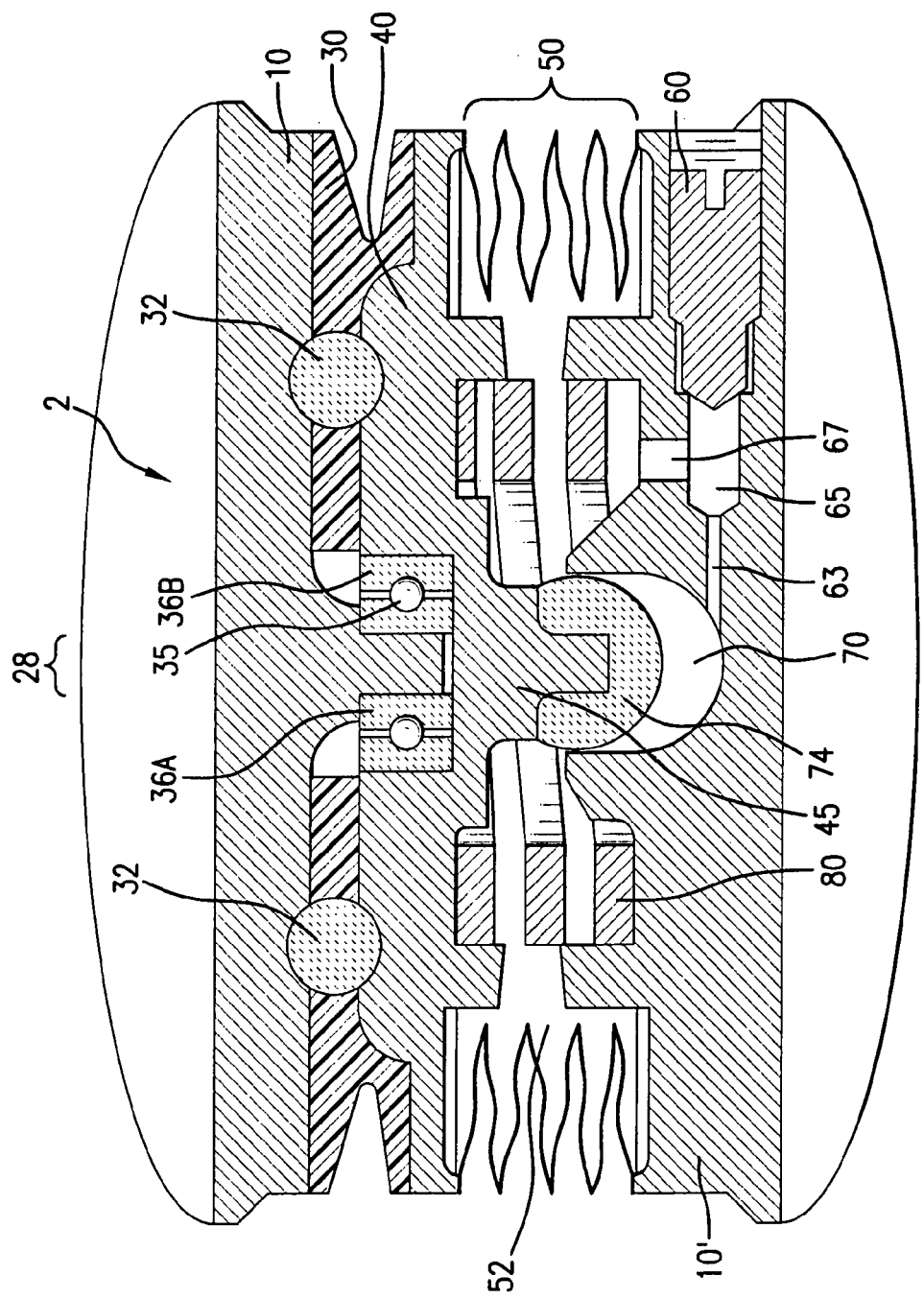
FIG. 7 is a cross-sectional view of an alternative non-modular embodiment of a hydraulic spinal disc prosthesis assembly.

The embodiment depicted in FIG. 7 of a non-modular prosthetic assembly 2 is intended primarily for cervical disc replacements. In place of the spike-like vertebral engaging members in other embodiments of the present invention, the cervical disc prosthesis has non-planar vertebra engaging surfaces, comprising a convex surface that can be seated into the relatively concave central area of the central vertebral endplates. This convex surface has a roughened texture, such as with the sintered surfaces of the flat vertebra engaging surfaces of the crown plates of the preferred embodiments. The adaptation of the top and bottom outer surfaces to a concave profile complementary to the anatomic vertebral endplate profile, a snug fit is achieved that maintains the prosthesis in proper position as bony ingrowth solidifies the connection between the disc prosthesis and opposing vertebrae.

Surgical Procedure

The particular crown plates 10, 10' and the particularly selected bellows cartridge 100 to be implanted in a specific patient are chosen by the surgical team so as to best accommodate the anticipated biomechanical demands of that particular patient's spinal disc replacement. Once the disc prosthesis components have been selected, the crown plates 10, 10' are connected to the bellows cartridge 100 by aligning and advancing cartridge 100 along the chined edges 6, 7 (as best seen in FIG. 4A) of the crown plates 10, 10' that complement the chined edges of the cartridge's end caps 20, 20'. This coupling is similar to dove-tail joinery used in cabinet making, for example, in a cabinet drawer. Once the assembly is accomplished for both opposing crown plates, the juxtaposition of the crown plates 10, 10' with cartridge 100 is fixedly secured by advancing pairs of set screws 96 and 96' (as in FIGS. 5A and 5C) into the threaded through holes 95A, 95B and 95'A, 95'B until the set screws 96 are seated in respective recess pairs 22A, 22'A of end caps 20 and 20' as shown in FIG. 3A.

With the spinal disc prosthetic modular assembly 1 thus assembled with selectable components chosen to optimize the biomechanics of the effected intervertebral space and joint, the prosthetic modular assembly 1, is attached to the insertion tool 300. Per FIGS. 4A and 1C, this is done by sliding the insertion tool's distal effector head 360 between the crown plates 10 so that the beveled edges of the insertion tool's distal surface matingly complement the beveled inner edges of the crown plate 6, 7; with the insertion tool effector head 360 juxtaposed against the opposed crown plates 10, 10' but not in contact with the bellows assembly 50. Threaded knob 350 is rotated so as to displace pawl pairs 369, 369' into the respective recesses 91, 91' in the crown plates 10. When the pawls are seated in their respective recesses, the insertion instrument 300 is reversibly coupled with the spinal disc prosthetic modular assembly 1.

In the preferred embodiment, the diseased spinal disc is surgically approached from the patient's anterior and the diseased disc is removed by surgical techniques well known to those skilled in surgical arts. A standard vertebral distracting instrument is used to sufficiently spread apart the adjacent vertebrae so as to accommodate the spinal disc prosthetic modular assembly 1. This standard vertebral distracting instrument has paired, opposing, detachable, interchangeable end pieces and the vertebrae are typically separated using a pair of rounded paddle attachments attached to the distracting instrument so that whatever force is necessary is applied over the largest possible surface area, thereby minimizing the risk of causing a vertebral endplate fracture or other trauma.

The space between the vertebral endplates accomplished by distracting the vertebrae should be wide enough for the crown plates 10, 10' to slide into, but not so the spikes 12 can clear the endplates. The spikes 12, 12' protruding from the vertebral engaging surfaces of the crown plates 10, 10' cuttingly engage the vertebral end plates during intra-operative positioning and placement of the prosthesis, thereby creating bony channels in the vertebral endplates, each channel extending from anterior to posterior.

Once the vertebrae are sufficiently distracted as described above, the distracting tool may be removed without fear of the vertebrae suddenly re-approximating; the vertebrae do not simply spring back into juxtaposition, vertebral re-approximation being a very slow process. At this point, the distracting paddles are detached and the upper and lower (cephalad and caudal) distraction bars 320 are fitted onto the standard distracting instrument. Each distracting bar 320, 320' is positioned in the midline of the respective vertebral end plates within the intervertebral space. The proper positioning and alignment of the prosthetic modular assembly 1 in the intervertebral space is crucial for the subsequent functioning of the spinal disc prosthetic modular assembly 1. Proper surgical placement of the distraction bars 320, 320' is confirmed by methods well known to the surgical arts, including but not limited to palpation, visual inspection, fluoroscopic and x-ray confirmation, and other stereotactic guiding measures well known to those skilled in the surgical arts.

The surfaces of the distraction bars 320, 320' are roughened in the same or similar way as are the vertebral engaging surfaces of the crown plates 10, 10' thereby allowing the distraction bars 320, 320' to better maintain their preferred positioning as determined by the surgical team. With the distraction bars 320, 320' in place and still connected to the standard distracting tool with its angled extension arm seen in FIGS. 1A and 1D, the spinal disc prosthetic modular assembly 1, coupled to insertion tool 300, is advanced along the distraction bars 320, 320' as the bars 320, 320' are slidingly received into through channels 14, 14'.

The advancement of the disc prosthetic modular assembly 1 into the intervertebral space requires some considerable force, as may be applied with a mallet or hammer or other such instrument. To avoid damaging the bellows cartridge assembly 100, the insertion tool 300 connectedly contacts the crown plates 10, 10' without making any contact with the bellows assembly 50; this is seen in the side view of the insertion tool 300 coupling with prosthetic modular assembly 1 in FIG. 1C. The forceful advancing of the prosthetic modular assembly 1 from anterior to posterior into position between the vertebrae causes the protruding spikes 12, 12' to carve a channel through the vertebral end plates as they are advanced posteriorly to the desired location. The apparently traumatic effect of the spikes 12, 12' creating their own channel in the bony surface of the vertebral end plates is considered surgically desirable insofar as heterotopic bone growth is thereby stimulated, promoting the eventual solid bony fixation of the prosthetic modular assembly 1 in place.

Once the spinal disc prosthetic modular assembly 1 is in the desired position, the insertion tool 300 is disconnected by reversing the connection of the pairs of pawls 369 and 369' in the recesses 91 and 91' respectively. Retraction of the pawls 369 from recesses 91, effected by rotation of the threaded knob 350, permits the insertion tool 300 to be withdrawn while leaving the prosthetic modular assembly 1 in place. The distraction bars 320 are then slidingly withdrawn along channels 14 and out of the intervertebral space, thereby leaving the spinal disc prosthetic modular assembly 1 as the only hardware left in place between the opposing vertebrae. The rest of the implantation, involving the surgical wound closure and so forth, is well known to those skilled in the surgical arts.

Although this invention has been described in connection with specific forms and embodiments thereof, it should be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

We claim:

1. A modular spinal disc prosthesis system for a surgical implantation of an individually optimized compressible, rotatable and tiltable hydraulic spinal disc prosthesis assembly between a pair of adjacent vertebrae, comprising:

(a) a pair of selectable opposed crown plate modules with chined edges, consisting essentially of a selectable cephalad crown plate module and a selectable caudal crown plate module, with each selectable crown plate module having a predetermined lordotic angle, a predetermined cross-sectional profile, with each of said selectable opposed crown plate modules being fixedly engageable with a vertebral endplate by a plurality of vertebra engaging members fixedly connected to a vertebra engaging surface of each of said selectable opposed crown plate modules;

(b) at least one selectable, compressible, rotatable and tiltable hydraulic disc prosthesis cartridge module, with each selectable disc prosthesis cartridge module comprising an axial load dampening mechanism of a predetermined size and a predetermined load-bearing capacity, wherein at least one selectable cartridge module is sandwiched connectedly between and coupled to said opposed selectable crown plate modules; and (c) an insertion instrument to facilitate the surgical implantation of said individualized spinal disc prosthesis assembly, wherein said individualized compressible, rotatable and tiltable hydraulic spinal disc prosthesis assembly, comprised of said selectable disc prosthesis cartridge module connectedly interposed between said pair of selectable opposed crown plate; wherein said axial load dampening mechanism comprises: (a) a compressible tiltable bellows assembly containing at least one fluid; (b) a dashpot assembly; and (c) at least one biasing member positioned within said bellows assembly in co-axial proximity to said dashpot assembly.

2. The modular spinal disc prosthesis system as recited in claim 1, wherein said insertion instrument further comprising a surgical insertion tool having a pair of detachable opposing insertion bars reversibly receivable in a respective slot channel formed on said vertebra engaging surface of said selectable crown plate modules to facilitate thereby the surgical implantation of said individually optimized compressible, rotatable and tiltable hydraulic spinal disc prosthesis assembly positioned between said detachable opposing insertion bars.

3. The modular spinal disc prosthesis system as recited in claim 1, wherein a bellows cartridge module further comprises:
(a) a compressible tiltable bellows assembly;
(b) a pair of opposed endcaps, comprising a cephalad endcap and a caudal endcap, said endcaps connectable to said respective crown plate modules, with said caudal endcap having formed therein at least one sealable fluid conduit fluidically connecting said fluid-tight bellows chamber to an exterior of said spinal prosthesis device;
(c) a center bearings plate being coupled on a caudal side thereof to a cephalad end of said bellows assembly and said caudal endcap being coupled to a caudal end of said bellows assembly, said center bearing plate and said caudal endcap, together defining therebetween a fluid-filled bellows chamber;
(d) a bearing retainer seal member having a radial thrust bearing assembly, said bearing retainer seal member being positioned between and rotationally coupled on a cephalad side to said cephalad endcap and on a caudal side, to said center bearings plate member;
(e) a dashpot assembly positioned between said caudal endcap and said center bearings plate and defining therein a dashpot chamber in fluid communication with said bellows chamber by said at least one sealable fluid conduit, wherein said fluid conduit comprises at least one orifice having a diameter sized to dampen a down stroke of a piston; and
(f) at least one biasing member fixedly positioned within said bellows assembly in co-axial proximity to said dashpot assembly.

4. The modular spinal disc prosthesis system as recited in claim 2, wherein the cross-sectional profile of each of said selectable crown plate modules is substantially congruent with a vertebral endplate to which said selected crown plate module is fixedly positioned.

5. The modular spinal disc prosthesis system as recited in claim 2, wherein said selectable cephalad crown plate module is provided with a first predetermined lordotic angle ranging from 0 degrees to 30 degrees, and said selectable caudal crown plate module is provided with a second predetermined lordotic angle ranging from 0 degrees to 30 degrees.

6. The modular spinal disc prosthesis system as recited in claim 5, wherein the cephalad crown plate module and the caudal crown plate module are fixedly positioned onto said respective endcaps of the bellows assembly by a screw threadingly advanced into a respective threaded through hole formed in said crown plate modules and received into a recess formed in said endcaps.

7. The modular spinal disc prosthesis system as recited in claim 5 wherein a vertebra engaging surface of said pair of selectable opposed crown plate modules includes a plurality of endplate engaging spike members projecting therefrom for securing said crown plate modules to the respective endplates of the adjacent vertebrae.

8. The modular spinal disc prosthesis system as recited in claim 3 wherein said center bearings plate member has a cephalad surface with an annular groove formed therein and said cephalad endcap has a corresponding annular groove formed on a caudal surface therein, and said cephalad endcap has a plurality of ball bearings received within a race formed by a juxtaposition of said annular groove of said cephalad endcap and said annular groove of said center bearings plate member.

9. The modular spinal disc prosthesis system as recited in claim 3, said dashpot assembly further comprising:
(a) a piston formed on an inner surface of said center bearings plate and protruding through a bore of a spherical bearing slidingly engaged to an outer surface of said piston and rotationally contiguous within a retaining ring element co-axial with and positioned inside said bellows assembly; and
(b) a dashpot recess formed on an inner surface of said caudal endcap to receive said piston therein, said dashpot recess being in fluid communication with said at least one fluid conduit, wherein said dashpot assembly is fixedly positioned centrally within and co-axial with said bellows assembly.

10. The modular spinal disc prosthesis system assembly as recited in claims 7 or 9, wherein said bearings are composed of a hard substantially inelastic material chosen from the group consisting of a ceramic, a metal, a high-density polymer, and a combination thereof.

11. The modular spinal disc prosthesis system as recited in claim 8, wherein said ceramic material comprises Silicone Nitride $Si_3 N_4$.

12. The modular spinal disc prosthesis system as recited in claim 3 wherein said compressible, rotatable and tiltable bellows assembly is pre-loaded according to the method comprising the steps of:
(a) providing a compressible tiltable bellows assembly having a bellows member with a cephalad opening and a caudal opening and formed from a plurality of washers sealingly connected edgewise one to another, and having a cephalad endcap and a caudal endcap fixedly attached to said openings respectively to define thereby a fluid-tight bellows chamber having at least one fluid conduit formed therethrough and fluidly connecting said bellows chamber to an exterior to allow ingress of a fluid in a subsequent filling operation;
(b) subsequently, compressing said bellows assembly to a predetermined full stroke excursion, and subsequently applying a constraining member to said compressed bellows assembly to maintain the assembly in a compressed condition;

(c) subsequently, fully immersing said compressed bellows assembly in a volume of at least one fluid;

(d) subsequently, exposing said immersed compressed bellows assembly to a predetermined sub-atmospheric pressure at a predetermined temperature under a vacuum condition so as to evacuate air from an interior of said bellows assembly;

(e) subsequently, admitting an atmosphere of pressure into the vacuum condition to cause thereby said immersed bellows assembly to fill with said at least one fluid;

(f) subsequently, returning said compressed fluid-filled bellows assembly to atmospheric pressure;

(g) subsequently, sealing said at least one fluid conduit with a sealing member; and (h) subsequently, uncompressing said bellows assembly to expand the assembly to a substantially no-load condition by releasing said constraining member maintaining the compressed condition of said bellows, whereby a biasing member positioned within the compressed bellows assembly exerts a distracting force to separate said caudal endcap from said cephalad endcap and thereby establish a predetermined sub-atmospheric pre-load pressure within said expanded pre-loaded bellows assembly.

13. The modular spinal disc prosthesis system as recited in claim 1, wherein the insertion instrument comprises:

(a) a handle assembly having a hand grip and a rotatable knob at a distal position;

(b) an elongate hollow shaft connecting said handle assembly proximally to an effector head, said effector head having a top surface and a bottom surface, and further having a respective pair of top and bottom proximal arcuate engaging edges provided with a substantially circular concave profile and a chined contour matingly complementary to said chined edges of the respective crown plate modules;

(c) an effector rod slidably positioned longitudinally within said elongate shaft and connecting said rotatable knob to at least one effector cam housed within said effector head;

(d) an upper pair of pawls and a lower pair of pawls, each of said paired pawls displaceably juxtaposed with at least one respective pair of lever arms in displaceable juxtaposition with said cam, with each pair of pawls positioned to be protrudingly displaceable through a respective pair of openings formed through a top and a bottom surface of said effector head, wherein rotation of said knob causes a displacement of said cam by a displacement of said effector rod, so as to displace said pawls through said respective openings, said pawls being received into a corresponding set of pawl recesses formed on at least one an inner surface of said opposed crown plate modules.

14. A method of preloading a compressible, rotatable and tiltable bellows assembly for an axial-load-bearing shear-resisting prosthetic device comprising the steps of:

(a) providing a compressible tiltable bellows assembly having a bellows member with a cephalad opening and a caudal opening and formed from a plurality of washers sealingly connected edgewise one to another, and having a cephalad endcap and a caudal endcap fixedly attached to said openings respectively to define thereby a fluid-tight bellows chamber having at least one fluid conduit formed therethrough and fluidly connecting said bellows chamber to an exterior to allow ingress of a fluid in a subsequent filling operation;

(b) subsequently, compressing said bellows assembly to a predetermined full stroke excursion, and subsequently applying a constraining member to said compressed bellows assembly to maintain the assembly in a compressed condition;

(c) subsequently, fully immersing said compressed bellows assembly in a volume of at least one fluid;

(d) subsequently, exposing said immersed compressed bellows assembly to a predetermined sub-atmospheric pressure at a predetermined temperature under a vacuum condition so as to evacuate air from an interior of said bellows assembly;

(e) subsequently, admitting an atmosphere of pressure into the vacuum condition to cause thereby said immersed bellows assembly to fill with said at least one fluid;

(f) subsequently, returning said compressed fluid-filled bellows assembly to atmospheric pressure;

(g) subsequently, sealing said at least one fluid conduit with a sealing member; and (h) subsequently, uncompressing said bellows assembly to expand the assembly to a substantially no-load condition by releasing said constraining member maintaining the mechanically compressed condition of said bellows, whereby a biasing member positioned within the compressed bellows assembly exerts a distracting force to separate said caudal endcap from said cephalad endcap and thereby establish a predetermined sub-atmospheric pre-load pressure within said expanded pre-loaded bellows assembly.

15. A unitary compressible, rotatable and tiltable hydraulic spinal disc prosthesis assembly for a surgical implantation between a pair of adjacent vertebrae, comprising:

(a) a cephalad crown plate member with a cephalad vertebral engaging surface formed with a convex profile to provide a substantially fixed complementary juxtaposition with a concave shape of a vertebral endplate;

(b) at least one center bearings plate member rotationally coupled to said cephalad crown plate member and further comprising a radial thrust bearing assembly;

(c) a caudal crown plate member hydraulically coupled to said center bearing plate member and having a caudal vertebral engaging surface formed with a convex profile to provide a substantially fixed complementary juxtaposition with a concave shape of a vertebral endplate;

(d) a bellows assembly having a bellows chamber defined therein, fixedly interposed between said caudal crown plate member and said center bearings plate member;

(e) a dashpot device for dampening axial force loads and for resisting shearing force loads between said cephalad crown plate member and said caudal crown plate member, being positionally located between said center bearings plate member and said caudal crown plate member within and coaxial with said bellows assembly; and (f) at least one biasing member in coaxial proximity with said dashpot device for further dampening axial force loads on said unitary compressible, rotatable and tiltable hydraulic spinal disc prosthesis assembly.

16. The unitary compressible, rotatable and tiltable hydraulic spinal disc prosthesis assembly for a surgical implantation between a pair of adjacent vertebrae as recited in claim 15, wherein said bellows chamber is provided with a pre-loaded sub-atmospheric pressure.

* * * * *